(12) United States Patent
Loibner et al.

(10) Patent No.: US 9,561,263 B2
(45) Date of Patent: Feb. 7, 2017

(54) TREATMENT OF INFLAMMATORY ILLNESSES WITH ACE2

(75) Inventors: Hans Loibner, Vienna (AT); Manfred Schuster, Schrick (AT)

(73) Assignee: Apeiron Biologics AG (AT)

( * ) Notice: Subject to any disclaimer, the term of this patent is extended or adjusted under 35 U.S.C. 154(b) by 826 days.

(21) Appl. No.: 12/808,818

(22) PCT Filed: Dec. 18, 2008

(86) PCT No.: PCT/AT2008/000460
§ 371 (c)(1),
(2), (4) Date: Oct. 14, 2010

(87) PCT Pub. No.: WO2009/076694
PCT Pub. Date: Jun. 25, 2009

(65) Prior Publication Data
US 2011/0020315 A1  Jan. 27, 2011

(30) Foreign Application Priority Data
Dec. 18, 2007  (AT) ................ A 2058/2007

(51) Int. Cl.
*A61K 38/48* (2006.01)
(52) U.S. Cl.
CPC ................ *A61K 38/4813* (2013.01)
(58) Field of Classification Search
None
See application file for complete search history.

(56) References Cited

U.S. PATENT DOCUMENTS

| | | | | |
|---|---|---|---|---|
| 6,900,033 | B2 * | 5/2005 | Parry et al. | 435/69.1 |
| 7,482,171 | B2 * | 1/2009 | Acton et al. | 436/501 |
| 7,842,709 | B2 * | 11/2010 | Tartaglia et al. | 514/400 |
| 2005/0147600 | A1 * | 7/2005 | Acton et al. | 424/94.64 |

FOREIGN PATENT DOCUMENTS

| | | | | |
|---|---|---|---|---|
| EP | 1 723 962 | * | 11/2006 | A61K 38/48 |
| WO | WO 02/098448 A1 | | 12/2002 | |

OTHER PUBLICATIONS

Guang et al (Arch. Cardio. Dis., 105:373-385 (2012).*
Imai et al (Nature, 436:112-116 (2005).*
Warner et al (JBC, 280(47): 39353-39362 (2005).*
BLAST Alignment of SEQ ID No. 1 (accessed Jun. 22, 2015).*
Gupta et al., Am. J. Physiol. Renal Physiol., 293:F245-254 (2007).*
Bucher et al., Hypertension, 38:177-182 (2001).*
Ferrario et al., Am. J. Physiol. Heart Circ. Physiol., 289: H2281-H2290 (2005).*
Nakamura et al., Cytokine, 11(10):759-765 (1999).*
Ferreri et al., Am. J. Physiologic. Soc., F148-F155 (1998).*
Arenas et al., Am J Physiol Cell Physiol 286:C779-C784 (2004).*
Patel et al., J. Mol. Cell. Cardio., 66:167-176 (2014).*
Danilczyk et al., Circ Res., 98:463-471 (2006).*
Bengtson et al., Blood, 108:2055-2063 (2006).*

(Continued)

*Primary Examiner* — Thomas J Visone
(74) *Attorney, Agent, or Firm* — William T. Han; Edward R. Gimmi

(57) ABSTRACT

The present invention relates to ACE2 for the therapeutic treatment or prevention of inflammation.

3 Claims, 7 Drawing Sheets

(56) References Cited

OTHER PUBLICATIONS

Farmer et al., Annu. Rev. Pharmacol. Toxicol., 32:511-536 (1992).*
Siebeck abstract (1989).*
Deshayes, et al., Angiotensin receptors: a new role in cancer? Trends in Endocrinology & Metabolism, vol. 16, No. 7, Sep. 2005, pp. 293-299.
Yu, et al., Journal of Molecular and Cellular Cardiology, Abstracts, vol. 42, pp. S37-S54, 2007.

* cited by examiner

SEQUENCE LISTING

```
<160> NUMBER OF SEQ ID NOS: 1

<210> SEQ ID NO 1
<211> LENGTH: 740
<212> TYPE: PRT
<213> ORGANISM: Homo sapiens

<400> SEQUENCE: 1

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
```

-continued

```
                20                  25                  30
Asn His Glu Ala Glu Asp Leu Phe Tyr Gln Ser Ser Leu Ala Ser Trp
             35                  40                  45
Asn Tyr Asn Thr Asn Ile Thr Glu Glu Asn Val Gln Asn Met Asn Asn
 50                  55                  60
Ala Gly Asp Lys Trp Ser Ala Phe Leu Lys Glu Gln Ser Thr Leu Ala
 65                  70                  75                  80
Gln Met Tyr Pro Leu Gln Glu Ile Gln Asn Leu Thr Val Lys Leu Gln
                 85                  90                  95
Leu Gln Ala Leu Gln Gln Asn Gly Ser Ser Val Leu Ser Glu Asp Lys
                100                 105                 110
Ser Lys Arg Leu Asn Thr Ile Leu Asn Thr Met Ser Thr Ile Tyr Ser
            115                 120                 125
Thr Gly Lys Val Cys Asn Pro Asp Asn Pro Gln Glu Cys Leu Leu Leu
            130                 135                 140
Glu Pro Gly Leu Asn Glu Ile Met Ala Asn Ser Leu Asp Tyr Asn Glu
145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
            180                 185                 190
Ala Asn His Tyr Glu Asp Tyr Gly Asp Tyr Trp Arg Gly Asp Tyr Glu
            195                 200                 205
Val Asn Gly Val Asp Gly Tyr Asp Tyr Ser Arg Gly Gln Leu Ile Glu
            210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
            260                 265                 270
Arg Phe Trp Thr Asn Leu Tyr Ser Leu Thr Val Pro Phe Gly Gln Lys
            275                 280                 285
Pro Asn Ile Asp Val Thr Asp Ala Met Val Asp Gln Ala Trp Asp Ala
290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
            340                 345                 350
Lys Gly Asp Phe Arg Ile Leu Met Cys Thr Lys Val Thr Met Asp Asp
            355                 360                 365
Phe Leu Thr Ala His His Glu Met Gly His Ile Gln Tyr Asp Met Ala
            370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
            435                 440                 445
```

-continued

```
Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser
            740
```

TREATMENT OF INFLAMMATORY ILLNESSES WITH ACE2

This application is a 371 of International Application No. PCT/AT2008/000460, filed 18 December 2008, which claims priority to A 2058/2007, filed 18 Dec. 2007, all of which are herein incorporated by reference in their entireties.

The present invention relates to the field of treatment of inflammatory diseases.

BACKGROUND OF THE INVENTION

An inflammatory response is a process in which defensive cells are produced on route to an infectious source and ensure the elimination of the cause there. Different mediator substances are released in this process, contributing to the elimination but also creating the inflammation symptoms. In cases of faulty regulation of the reaction, these symptoms may cause most of the damage and/or may be the source of disease in general (e.g., in the case of allergies). A differentiation may also be made between acute inflammations (such as sepsis) and latent chronic inflammations (such as rheumatism). Inflammations may also be artificially induced, e.g., in organ transplants, which may ultimately result in rejection of the foreign organ. Inflammations may also be induced as an adverse effect due to certain medications.

In all these states, an artificial regulation of the immune response may be appropriate either as the main treatment or to nearly relieve symptoms.

During an inflammation, a number of cytokines may play a definite role in the progression of an immune response. Activated CD4-T cells produce interleukin-2, which is essential for activation of CD8-T cells as well as B cells. In addition, CD4-T cells produce other cytokines such as IFN-gamma, which enhances macrophage activity. TFN-alpha regulates the activity of different immune cells and may stimulate cell death, cell proliferation, cell differentiation, and secretion of other cytokines. It plays a triggering role in symptoms such as fever in particular.

One goal of the present invention is to make available an immune system regulator, in particular for treatment of inflammations.

The present invention therefore relates to a protein or a nucleic acid encoding the protein, where the protein is ACE2, for therapeutic treatment or prevention of an inflammation (or inflammatory diseases). Likewise, the present invention relates to the use of an ACE2 protein or an ACE2-encoding nucleic acid for production of a pharmaceutical composition for treatment or prevention of an inflammation. This likewise provides for the use of ACE2 protein or an ACE2-encoding nucleic acid for immunomodulation in a patient, such as treatment or prevention of an inflammation.

Angiotensin-converting enzyme 2 (ACE2) is an essential enzyme of the renin-angiotensin-aldosterone system, which is expressed as a membrane-anchored glycoprotein on various organs such as the heart, kidneys, liver, and lungs, but also on blood vessels.

ACE2 was discovered in 1997 as an ACE-homologous enzyme (GenBank Acc.: BAB40370, encoded by a nucleic acid with the sequence according to GenBank Acc.: AB046569). Initially it was thought to have the same enzymatic activity as ACE (U.S. Pat. No. 6,989,363). Only later was it discovered that ACE2 has a completely different mechanism of action than ACE and is even antagonistic to it (WO 2004/000367). ACE2 is a carboxypeptidase which cleaves numerous peptide substrates with great differences in selectivity and activity. ACE2 is also a cellular binding partner of SARS coronaviruses. Downregulation of ACE2 or administration of ACE2 to block virus receptors can therefore reduce susceptibility of ACE2-presenting cells (WO 2006/122819, Lang et al., Virology (2006) 353 (2): 474, Abstract). The functions described for ACE2 include mainly the conversion of Ang II to Ang 1-7, where the substrate and the product of this reaction have antagonistic properties. Ang II has essentially vasoconstrictive and hypotensive effects. Ang 1-7 has vasodilating effects and a protective effect in diseases of the heart, lungs, and kidneys (WO 2004/000367).

SUMMARY OF THE INVENTION

The ACE2 product Ang 1-7 also inhibits ACE, the enzyme responsible for production of Ang II. Expression of ACE2 is controlled by various stimuli. It has now been found that ACE2 is downregulated by the occurrence of inflammatory cytokines such as TNF-alpha, IFN-gamma, or IL-4, which subsequently leads to various diseases and to an accumulation of Ang II in the respective compartments and leads to a potentiation of the immune response that has been initiated. Cytokines are essentially for communication among various types of cells of the immune system. One of the first steps of a nascent inflammation usually consists of antigenic substances being taken up by antigen-presenting cells (APCs) and classified as foreign. Subsequently there is an initial output of inflammatory cytokines by the respective APCs, which thereby alarm the additional cells of the immune system. This mechanism is highly regulated and controlled to initiate an immune response only when it is actually justified and to switch it off again when the antigenic substance has been neutralized. Nevertheless it may happen that once this immune response has been initiated, it goes out of control and turns against one's own body. The accumulation of Ang II, e.g., in various renal, cardiac, and pulmonary diseases due to a progressive inflammation and increased infiltration of the respective tissue by cells of the immune system and subsequently leads to an overshooting immune response. One example is sepsis, where very large quantities of inflammatory cytokines are secreted and an immune response is initiated systemically, leading to massive damage of virtually all organs. Furthermore, an allergic attack or outbreak of an autoimmune disease can also be treated or prevented. However, a key point here is always the cellular immune response as a response to a stimulus, which by far overfulfills the primary purpose of neutralizing a foreign substance in a potentiating amplification cascade and then subsequently damages the body.

The first step in the incipient immune response is to send out inflammatory signals in the form of cytokines. The main representatives thereof are IL-4, IFN-gamma, or TNF-alpha, for example. Substances having the property of suppressing or weakening this cytokine expression after stimulation of the immune cell are usable therapeutic agents for attenuating an overshooting immune response. ACE2 expression drops sharply in the presence of inflammatory cytokines on a cellular level, leading to potentiation of the inflammation, especially due to an accumulation of Ang II, due to a reduction in Ang 1-7 and due to the resulting lack of a reduction in Ang II reformation (FIG. 1). The resulting great increases in Ang II concentrations therefore further potentiate the inflammation due to the strong inflammatory properties of Ang II, further leading to an even greater attenuation of ACE2 expression. To break this vicious cycle, ACE2 is administered therapeutically according to the present invention, thus preventing an accumulation of Ang II and thereby reducing the inflammation. ACE2 directly prevents high Ang II titers, thus diminishing the constantly increasing inflammation due to Ang II. Ang 1-7 is formed again and also diminishes the inflammation through its anti-inflammatory effect. Furthermore, Ang 1-7 limits the subsequent production of Ang II through its property of inhibiting ACE. The subsidence of the inflammation causes the cytokines that have been excreted to return to a normal level, which again results in endogenous ACE2 expression, thus ensuring the degradation of Ang II in the long run and ensuring the development of Ang 1-7 and also leading to a stable functional RAS. In the remaining course, a self-regulating independent equilibrium among the interacting components of the RAS is again reestablished. Renewed administration of ACE2 may thus be omitted entirely if the original stimulus of the immune system has been neutralized. FIG. 1 shows a schematic diagram of the mechanisms mentioned here. Administration of ACE2 creates a way out of the potentiating inflammation.

The inflammation is preferably a local inflammation of a tissue or organ and/or a systemic inflammation. In addition, based on the general mechanism, it is possible to treat both chronic and acute inflammations. In particular, the inflammation may include rheumatitis, sepsis, arthritis, rheumatoid systemic lupus erythematosus, or scleroderma. These may be caused by mechanical or chemical cellular damage or tissue damage or wounds, infections, in particular pathogens such as viruses, bacteria, or fungi, by implants including organ implants and by medications.

The inflammation may also comprise an autoimmune disease. The disease may be, for example, an antiglomerular basal membrane disease, autoimmune diseases of the nervous system, systemic lupus erythematosus, Addison's disease, an antiphospholipid syndrome, an IgA glomerulonephritis, a Goodpasture syndrome, a Lambert-Eaton myasthenic syndrome, idiopathic purpura, an autoimmune thyroiditis, a rheumatoid arthritis, an insulin-dependent diabetes mellitus, an pemphigus, an autoimmune hemolytic anemia, a dermatitis herpetiformis Durhing, a membranous glomerulonephritis, a Graves disease, a sympathetic ophthalmia, autoimmune polyendocrinopathies, multiple sclerosis and/or Reiter's disease.

ACE2 is preferably used in the form of ACE2 protein, in particular as recombinant ACE2. ACE2 sequences are sufficiently well-know and can be produced with no problem by introducing suitable vectors that code for ACE2 into expression systems, in particular eukaryotic systems. Such systems include, for example, mammalian cell lines such as CHO (Chinese hamster ovary) cells and NSO mouse cells or insect cells, e.g., Sf9. For expression, such a vector may have certain cell-specific or general promoters.

The protein (for which the ACE2 nucleic acid also encodes) is preferably water-soluble ACE2, in particular without membrane domains. The human ACE2 sequence is given by SEQ ID No. 1:

The autologous signal sequence (underlined) is split off by the host cell for removal. The inventive ACE2 protein therefore comprises an ACE2 sequence that corresponds to SEQ ID No. 1 starting in position 18. In further embodiments, the ACE2 polypeptide does not have any transmembrane domains. These transmembrane domains are on the C-terminus of SEQ ID No. 1. Therefore, this is soluble ACE2. Especially preferred embodiments include soluble ACE2 polypeptides, whose polypeptide chain from the amino acids includes SEQ ID No. 1 up to amino acid position 740, or enzymatically active fragments thereof. Another soluble ACE2 protein consists of amino acids 18-615 of SEQ ID No. 1.

The solubility of a protein is determined not only by its amino acid sequence but also by its folding and by post-translational modifications. These are mainly charged sugar structures, which increase the solubility of a protein and influence its pharmacological profile. The soluble segment of ACE2 contains seven N-glycosylation sites. Preferably at least 80% of the N-glycosylation positions are glycosylated and/or the ACE2 protein has a sugar component of more than 10% (percent by weight of the total ACE2) or 11%, 12%, 13%, 14%, preferably greater than 15% or 16%, 17%, 18%, 19%, in particular greater than 20% or 21%, 22%, 23%, 24%, or 25%.

Although human ACE2 is preferred for most embodiments, ACE2 is also enabled by mouse, rat, hamster, pig, primate, or cattle. ACE2 is a universal enzyme in all mammals having the identical substrate Ang II. It can therefore also be used in foreign organisms. Humans, mice, rats, hamsters, swine, primates, or cattle may thus be treated with the inventive protein (or its nucleic acid) independently of the origin of the ACE2.

According to the invention, a pharmaceutical composition comprising the ACE2 protein or an ACE2-encoding nucleic acid may be made available according to the invention. Such compositions may include pharmaceutically suitable salts thereof, plus buffers, tonicity components or pharmaceutically suitable vehicles. In particular ACE2 nucleic acid may be provided in suitable therapeutic vector systems. Pharmaceutical vehicle substances are used to improve the tolerability of the composition and allow a better solubility as well as better bioavailability of the active substances. Examples here include emulsifiers, thickeners, redox components, starch, alcohol solutions, polyethylene glycol, or lipids. The selection of a suitable pharmaceutical vehicle depends to a great extent on how the substance is administered. Liquid or solid vehicles may be used for oral administration, but for injections the final composition must be a liquid.

The medication to be used according to the present invention comprises buffer substances or tonic substances. By means of buffers, the pH of the medication can be adjusted to physiological conditions and furthermore fluctuations in pH can be diminished and/or buffered. One example of this is a phosphate buffer. Tonic substances are used to adjust the osmolarity and may include ionic substances, for example, inorganic salts such as NaCl or non-ionic salts such as glycerol or carbohydrates.

The composition to be used according to the present invention is preferably prepared to be suitable for systemic, topical, oral, or intranasal administration. These forms of administration of the medication according to the present invention allow a rapid and uncomplicated uptake. For oral administration, for example, solid and/or liquid medications may be taken directly or dissolved and/or diluted.

The medication to be used according to the invention is preferably prepared for intravenous, intra-arterial, intramuscular, intravascular, intraperitoneal or subcutaneous administration. For example, injections or transfusions are suitable for this purpose. Administration directly into the bloodstream has the advantage that the active ingredients of the medication are distributed throughout the entire body and rapidly reach the target tissue.

The present invention is also illustrated by the following figures and examples without being limited to them.

DETAILED DESCRIPTION OF THE INVENTION

Examples

Example 1

Loss of ACE2 Expression in the Presence of Inflammatory Cytokines

Figure 1:
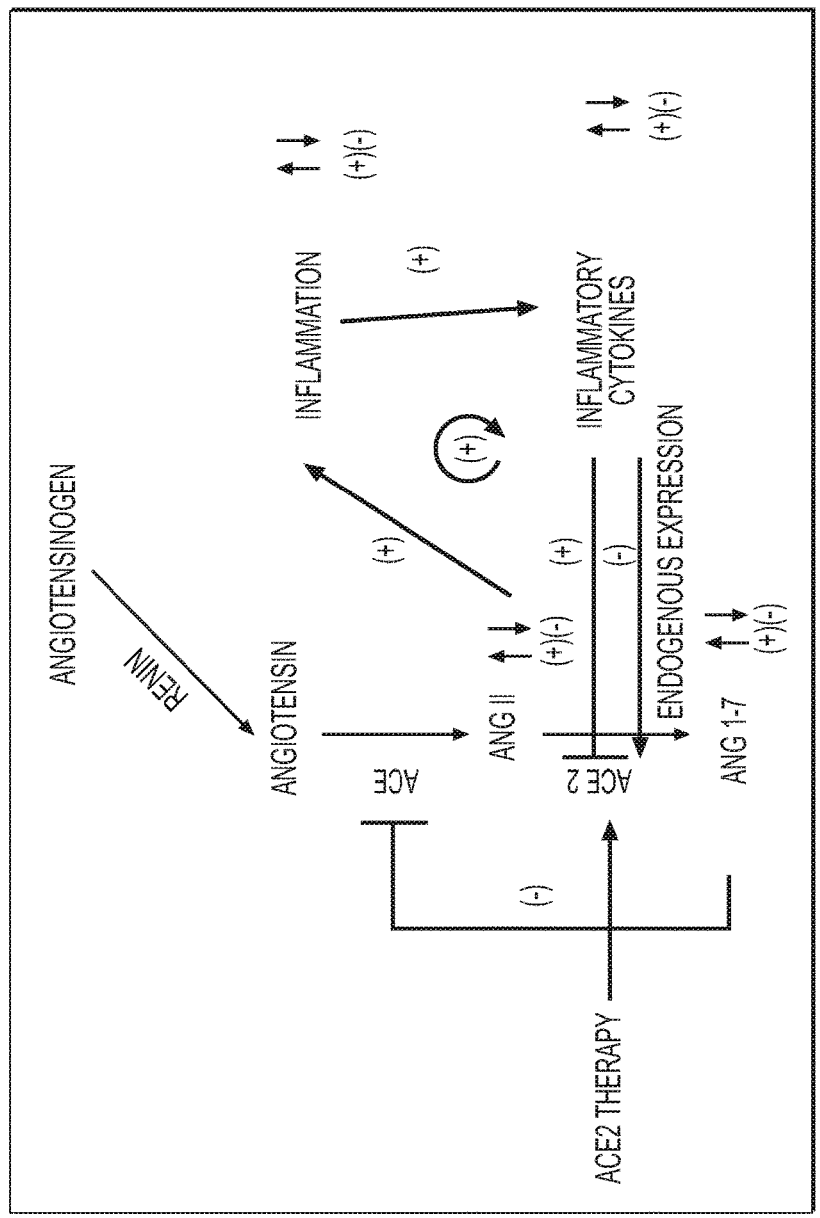
FIG. 1: Schematic diagram of the restoration of a functional RAS by ACE2 therapy. Red (+) arrows denote effects of the increasing immunoreactivity, while blue (−) arrows denote changes due to the ACE2 therapy.
Figure 2A:
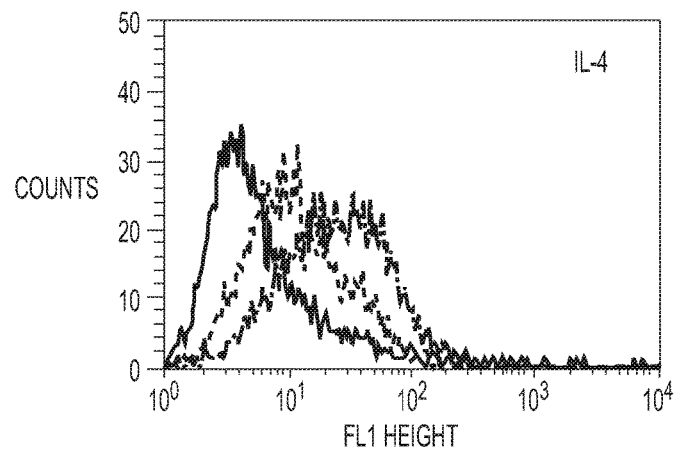
FIG. 2: ACE2-specific FACS analysis of Vero E6 cell preparations after incubation for 48 hours with 10 ng/mL IL-4 (A), IFN-gamma (B) or TNF-alpha (C) (curves with a middle peak) in comparison with an unstimulated control group (red curves with a peak on the right) and a control series (black curves with a peak on the left).
Figure 2B:
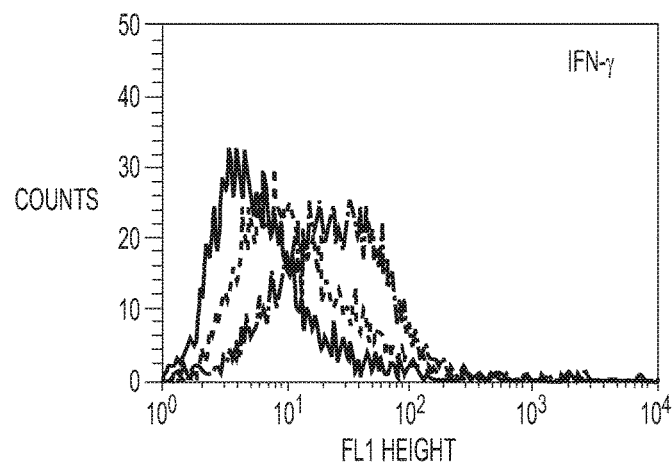
Figure 2C:
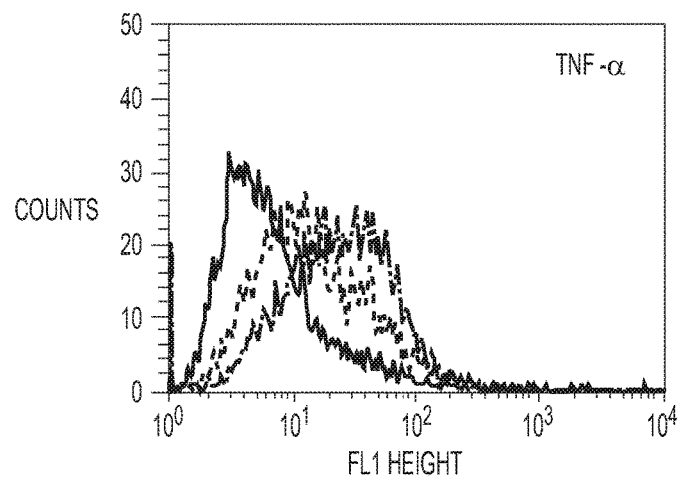

The renal cell line (Ceropithecus aethiops) Vero E6 expresses ACE2 as a membrane-anchored glycoprotein under the usual culture conditions. Vero E6 cells were incubated for 48 hours with 10 ng/mL IL-4, IFN-gamma or TNF-alpha and changes with regard to ACE2 surface expression were analyzed by FACS analysis using a polyclonal ACE2-specific goat antibody and a goat-specific FITC-labeled antibody. FIG. 2 shows the respective histograms. Table 1 summarizes the respective analysis. ACE2 expression is definitely reduced by incubation with IL-4, IFN-gamma or TNF-alpha. Although an ACE2 positivity of 51±3% was measured in unstimulated cells, this was reduced to 28±2%, 22±1% and 39±2%, respectively, in comparison with an unstimulated control group after incubation of Vero E6 for 48 hours with 10 ng/mL IL-4, IFN-gamma or TNF-alpha.

| Stimulation | IL-4 | IFN-gamma | TNF-alpha | Ø |
|---|---|---|---|---|
| Positivity | 28 ± 3% | 22 ± 1% | 39 ± 2% | 51 ± 3% |
| Negative controls | 5 | 2 | 4 | 6 |

Example 2

Attenuation of the Immune Reactivity of PBMCs

Figure 3:
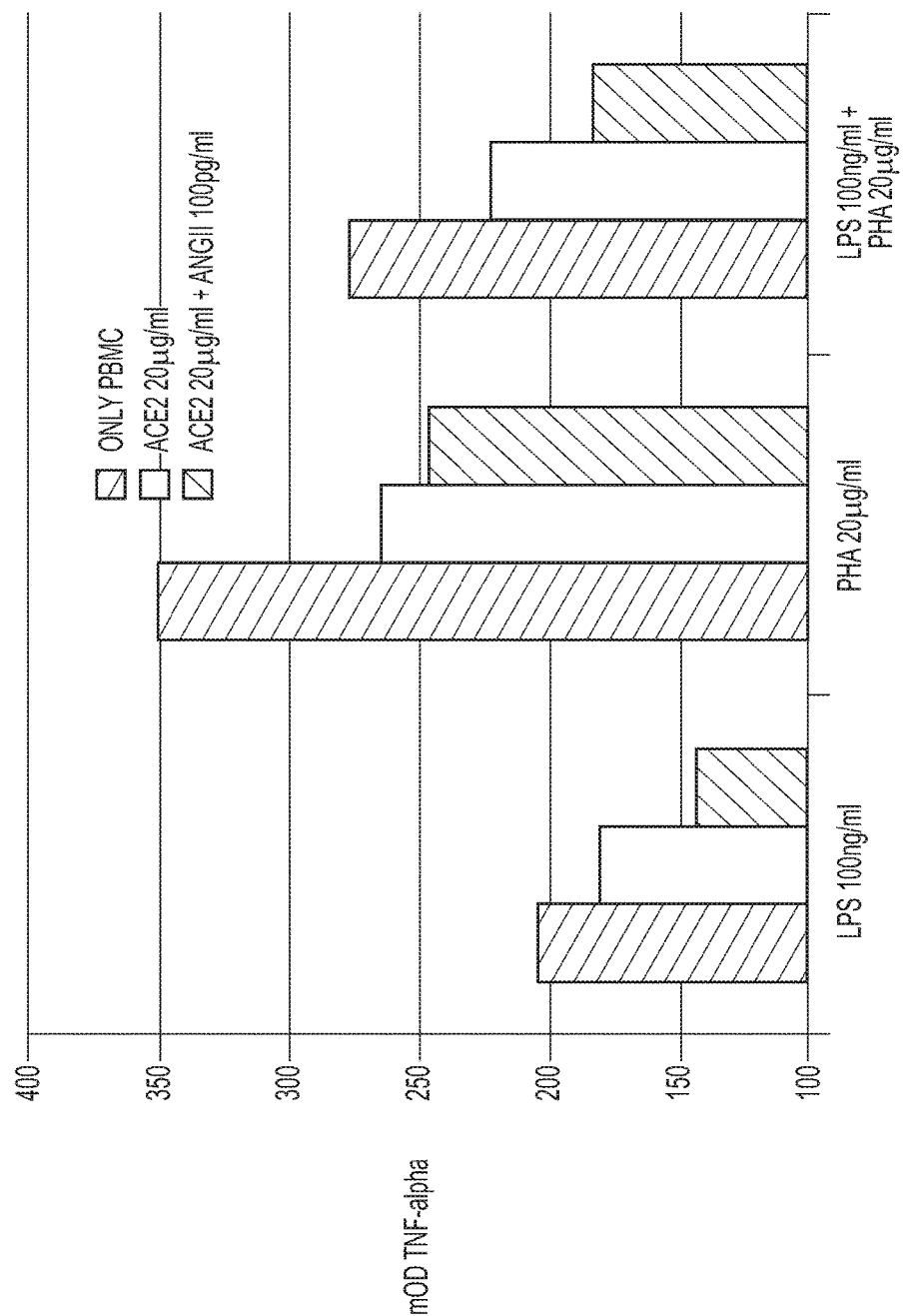
FIG. 3: Measurement of TNF-alpha in PBMC cultures supernatants 16 hours after stimulation with LPS, PHA and LPS+PHA, without ACE2 (black bar, left) and in the presence of the ACE2 (gray bar, center) or ACE2 and Ang II (blue bar, right).

In this example, the effect of ACE2 on cytokine expression of stimulated PBMCs (peripheral mononuclear blood cells) is explained. A PBMC preparation and thus the entire lymphocyte spectrum of the donor in the batch were used to allow the interaction of different lymphocytes. Whole blood was taken from a healthy donor and the PBMCs in that blood were separated by centrifugation. These cells were subsequently stimulated with strong immunogenic substances such as lipopolysaccharide (LPS, 100 ng/mL) and phytohemagglutinin (PHA, 20 µg/mL) and a combination of the two substances in the presence of Ang II, ACE2, and ACE2 with Ang II and then incubated for 16 hours at 37° C. The supernatants were tested for TNF-alpha and compared with a control batch, which was performed in the absence of ACE2 and peptides of RAS. The results of this experiment are plotted graphically in FIG. 3: incubation with LPS and HPA in all cases induced secretion of TNF-alpha. The respective control batches, which were co-incubated without ACE2, showed the highest TNF-alpha concentration (203, 352 and 278 mOD) each after LPS, PHA and combination stimulation. In the presence of ACE2, the measured signal was definitely lower in all groups, reaching mOD values of only 181, 266, 233 in the respective groups. In the presence of ACE2 and Ang II, however, the measured TNF-alpha concentrations were the lowest, reaching only mOD 144, 247 and 183. These results show that the presence of ACE2 leads to a definitely reduced production of inflammatory cytokines, even if especially immunogenic substances such as LPS or PHA are used for stimulation. This confirms an anti-inflammatory effect of ACE2. Surprisingly, the mechanism also functions in the absence of Ang II and is potentiated in its presence, which thus indicates a dual principal. A portion of the effect is achieved by Ang II and its degradation product Ang 1-7, but another portion evidently functions by degradation of one of the other ACE2 substrates and is not bound to the ACE2 that is present (FIG. 3).

Example 3

Restoring the ACE2 Titer of the Healthy Body

Figure 4:
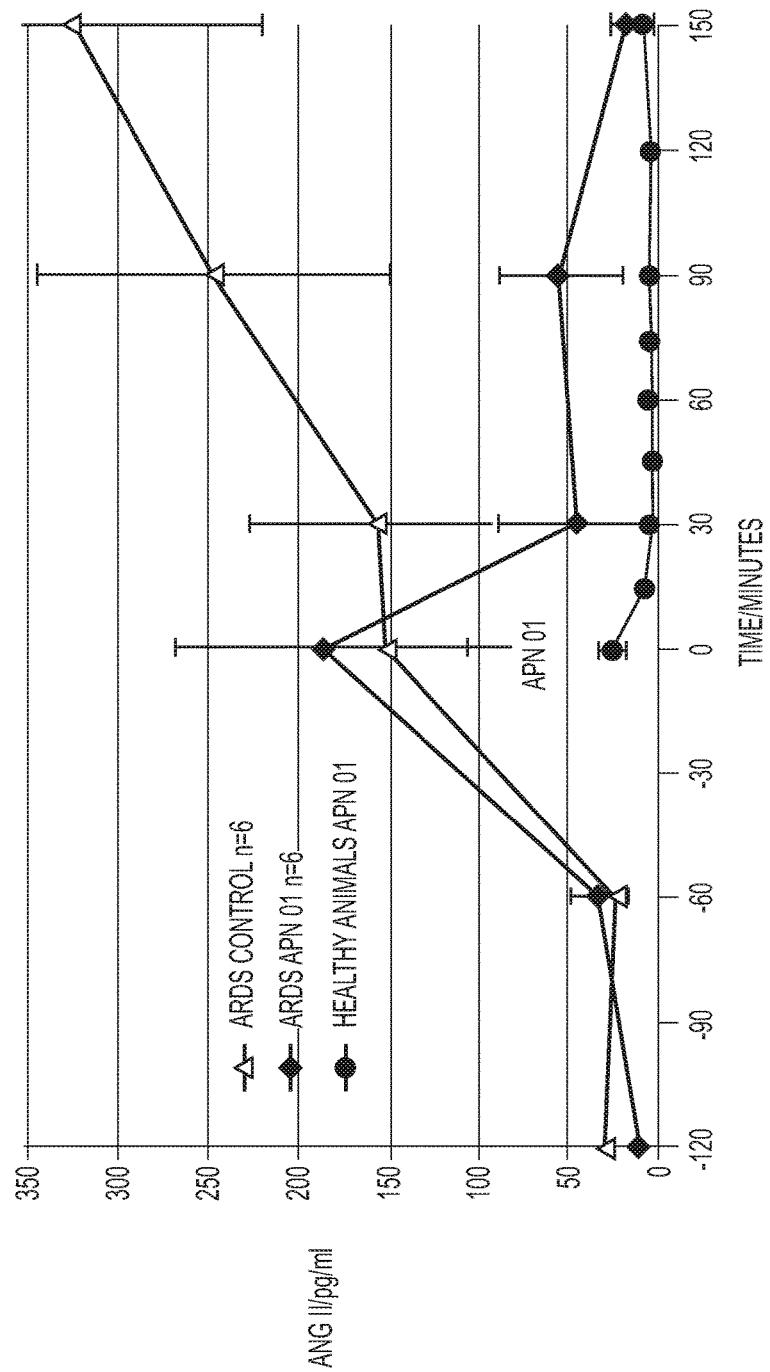
FIG. 4: Measured Ang II concentrations in a LPS-induced sepsis model in swine: blue curve: animals treated with APN 01 (rACE2); gray curve: animals treated with a placebo; gray curve (black dots): healthy animals after administration of APN 01.

This example demonstrates how administration of exogenous ACE2 brings a deregulated RAS back under control. APN 01 (recombinant soluble human ACE2) was therefore administered in a sepsis model induced by administration of LPS. LPS was infused into the animals continuously starting at the time −120 minutes, which led to a massive inflammation and subsequently to sepsis. Owing to the massive secretion of inflammatory cytokines, ACE2 expression ceased, which subsequently led to an accumulation of the inflammatory peptide ACE2 (see FIG. 4).

Figure 5:
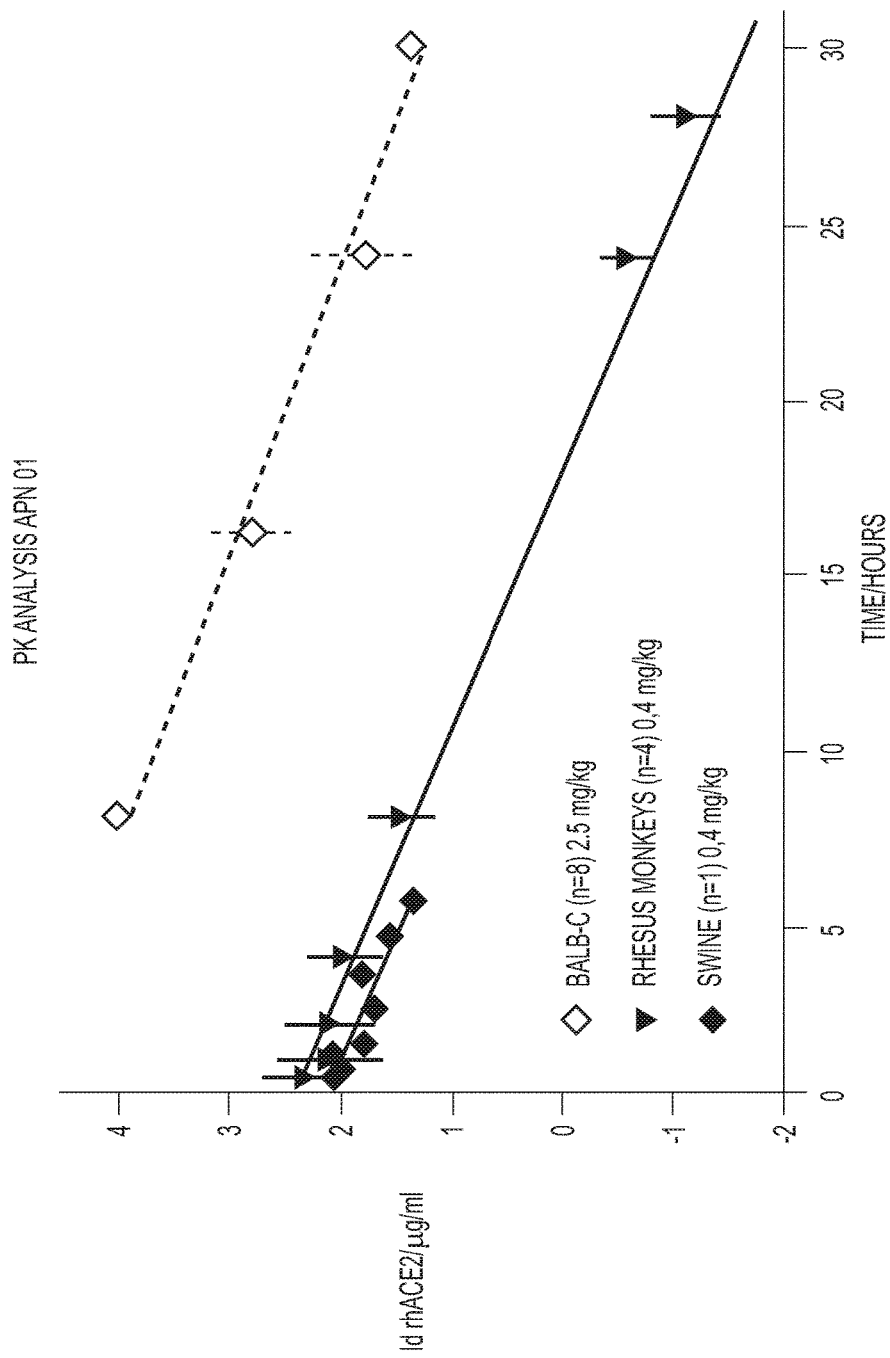
FIG. 5: Measured ACE2 activity in the mouse, pigs, and Rhesus macaques.

Starting at the time 0 minutes, APN 01 was administered intravenously as a bolus in a dose of 400 µg/kg. Immediately there was a drop in ACE2 in the treated group and the Ang II titer fluctuated within the following hour at the same level, which was also measured in the healthy animals. Furthermore, administration of APN 01 in the same dose to healthy animals also resulted in a brief decline in the ACE2 titer, which also approximated the values of the healthy animals after another hour. However, animals treated with a placebo showed a further increase in Ang II level until the end of the experiment. This surprising phenomenon can be explained only by restoration of the upregulated RAS, because active enzyme was available to the animals systemically until the end of the experiment (see FIG. 5). A half-life of approximately 8 hours was measured.

Example 4

Attenuation of the Expression of Inflammatory Cytokines in Sepsis

Figure 6:
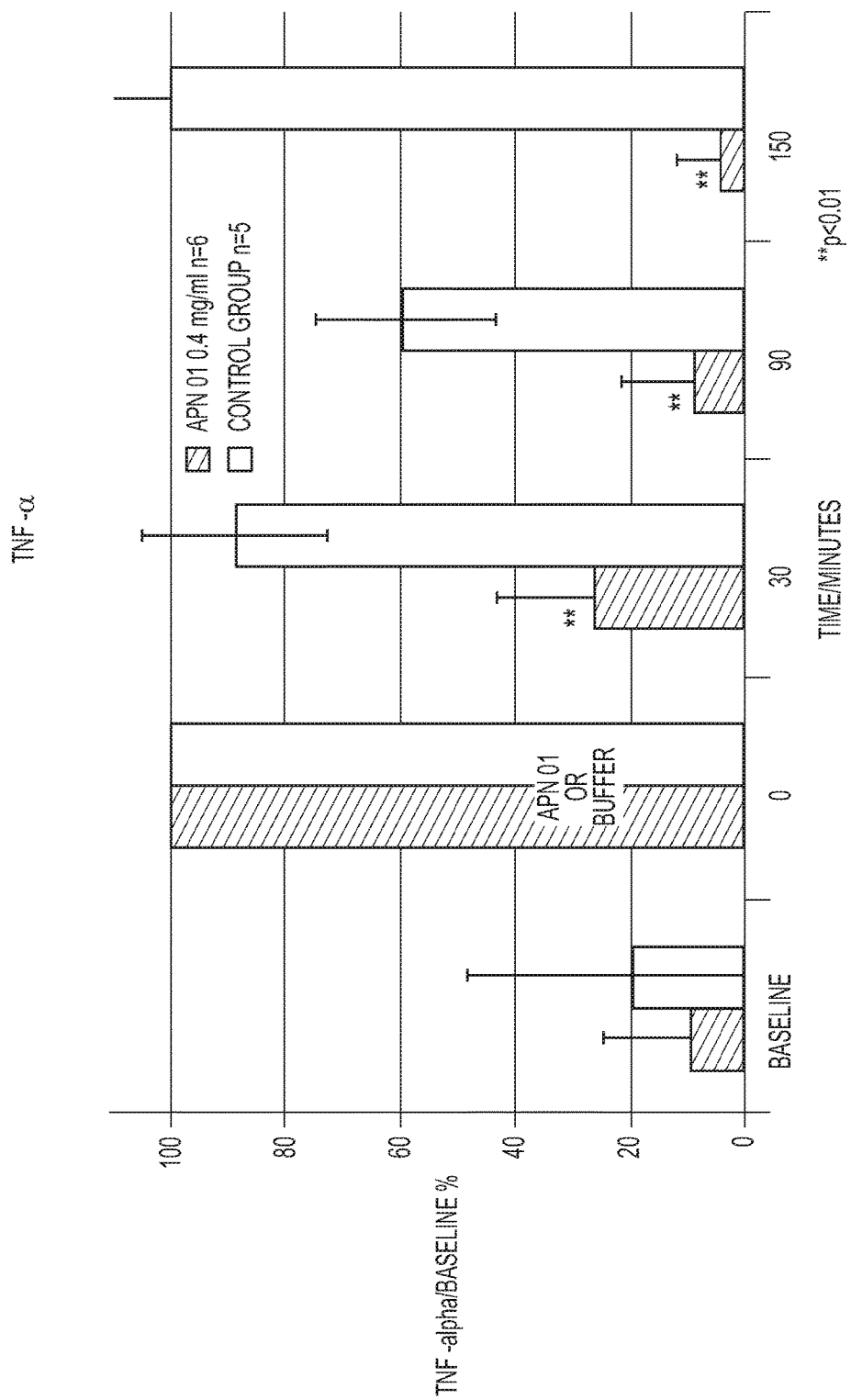
FIG. 6: Serum TNF-alpha concentration in an LPS-induced sepsis model in pigs. Animals treated with ACE2 are shown in gray. TNF-alpha concentrations have been standardized to the respective starting values at the start of treatment (100%).

The following example demonstrates how the concentration of the inflammatory cytokine increases rapidly in a sepsis model in swine and drops back to the level of healthy animals after administration of ACE2. Starting at the time −120 minutes, LPS was administered to the animals continuously in a high dose, leading to a massive inflammatory and subsequently to sepsis. Because of the massive secretion of inflammatory cytokines, this resulted in a reduction in ACE2 expression, which subsequently led not only to an accumulation of the inflammatory peptide Ang II but also the inflammatory cytokine TNF-alpha (FIG. 6). Starting at time 0 minutes, either ACE2 in a dose of 0.4 ng/kg or buffer solution was administered as a bolus to the animals (six animals in the treated group, 5 animals in the control group). While LPS was still being administered continuously in the same high dose, the animals were observed for three more hours and serum specimens were taken and analyzed for TNF-alpha. It was demonstrated that the TNF-alpha concentration in the control group remained elevated until the end of the experiment, whereas there was a definite reduction ($p<0.001$) in TNF-alpha concentration in the group treated with ACE2 already after a single dose of ACE2 and with continued administration of LPS. Despite massive sepsis, approximately the same values were again achieved as those also measured in healthy animals. Therefore the TNF-alpha expression can be rapidly reduced to the level of a healthy organism by administration of ACE2 even in a very aggressive sepsis model, and a further potentiating inflammation could be stopped (FIG. 6).

Example 5

Figure 7:
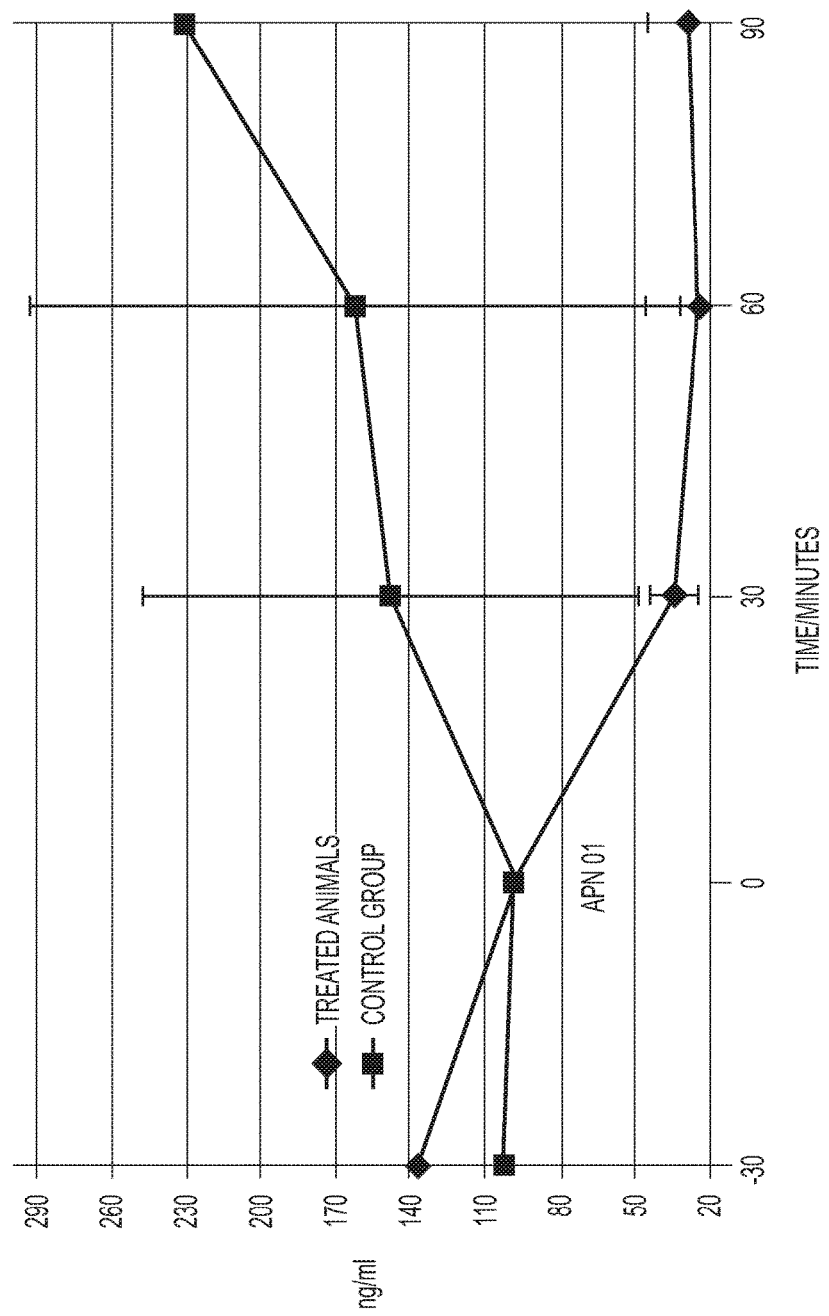
FIG. 7: Serum TNF-alpha concentration in swine in an ARDS model induced by aspiration of meconium. Animals treated with ACE2 are shown in blue, animals treated with a placebo are shown in gray.

Attenuation of Expression of all Inflammatory Cytokines after Local Mechanical Lung Damage In this example the influence of systemically administered ACE2 on the expression of inflammatory cytokines was demonstrated in a lung damage model in swine. Fourteen animals were taken into account in this blinded placebo-controlled study. All animals were subjected to aspiration of a 20% meconium solution three times in the first phase of the experiment, with comparable damage being induced in all animals on the basis of the hemodynamic parameters measured. In a second phase of the experiment, the therapeutic phase, recombinant soluble human ACE2 was administered intravenously as a bolus in a dose of 0.4 mg/kg to one-half of the animals. The other half received a physiological saline solution. Serum samples were taken at the times −30, 0, 30, 60, 90 and 150 minutes and used to measure the concentrations of the most important inflammatory cytokines. The time 0 was the starting point of the treatment at which time all animals were already manifesting ARDS symptoms. As illustrated in FIG. 7, there is a very definite influence of administration of ACE2 on the serum concentration of TNF-alpha. Although this rises markedly in the placebo group to more than 230 ng/mL, it drops in the treated group to less than 40 ng/mL within 30 minutes after administration, approaching 25 ng/mL 90 minutes after administration.

Example 6

Discussion

The data presented allow the following conclusions regarding the effect of ACE2 as an immunoregulator. Due to an antigenic stimulus, inflammatory cytokines are secreted. In the presence of inflammatory cytokines, there is a loss of ACE2 expression. In the absence of ACE2 the proinflammatory peptide Ang II accumulates because it cannot be degraded by ACE2. In the absence of ACE2, the proinflammatory cytokine TNF-alpha also accumulates. ACE2 has anti-inflammatory properties and reduces the expression of inflammatory cytokines in lymphocytes. Therefore, therapeutic administration of ACE2 compensates for the lost endogenous ACE2 expression and can combat an incipient inflammation by reducing Ang II titers, by forming Ang 1-7 and by other effects. Therapeutic administration of ACE2 in a case of severe sepsis even makes it possible to reduce the Ang II titer back to the level of a healthy person with continuous infusion of LPS and to restore the regulation of the RAS accordingly. Therapeutic administration of ACE2 also allows the TNF-alpha titer to be reduced back to the that of a healthy person in a case of severe sepsis with continuous infusion of LPS. The same effect has also been observed in a case of mechanical massive lung damage due to aspiration of meconium.

The invention claimed is:

1. A method of treating sepsis in a human subject in need thereof, comprising administering to a human patient in need thereof a water-soluble, recombinant, human angiotensin converting enzyme 2 (ACE2) polypeptide wherein said water-soluble, recombinant, human ACE2 polypeptide comprises amino acids 18-615 of SEQ ID NO:1, said ACE2 polypeptide is administered systemically.

2. The method of claim 1, wherein the ACE2 polypeptide comprises a polypeptide comprising amino acids 18 to 740 of SEQ ID No:1.

3. The method of claim 2, wherein the ACE2 polypeptide is glycosylated and has a sugar content of greater than 20% by weight of the total ACE2.

* * * * *